US009412259B2

(12) United States Patent
Nagase et al.

(10) Patent No.: US 9,412,259 B2
(45) Date of Patent: Aug. 9, 2016

(54) MEDICAL ALARM SYSTEM AND MEDICAL ALARM INDICATOR (71) Applicant: NIHON KOHDEN CORPORATION, Tokyo (JP)

(72) Inventors: Kazuya Nagase, Tokyo (JP); Rie Muneshima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 82 days.

(21) Appl. No.: 14/204,263

(22) Filed: Mar. 11, 2014

(65) Prior Publication Data

US 2014/0266709 A1 Sep. 18, 2014

(30) Foreign Application Priority Data

Mar. 12, 2013 (JP) .................. 2013-048666

(51) Int. Cl.
*G08B 1/08* (2006.01)
*G08B 25/10* (2006.01)
(Continued)

(52) U.S. Cl.
CPC ............... *G08B 25/10* (2013.01); *A61B 5/002* (2013.01); *A61B 5/742* (2013.01); *A61B 5/746* (2013.01); *G06F 19/327* (2013.01); *G06F 19/3418* (2013.01); *G08B 25/001* (2013.01); *G06K 9/00221* (2013.01)

(58) Field of Classification Search
CPC .... G08B 1/08; G08B 19/327; G08B 19/3418; G08B 9/00221
USPC .............. 340/539.1, 539.13, 539.11, 573.1
See application file for complete search history.

(56) References Cited

U.S. PATENT DOCUMENTS 5,561,412 A 10/1996 Novak et al.
5,696,492 A 12/1997 Sakamaki et al.
(Continued)

FOREIGN PATENT DOCUMENTS

JP 2000517114 A 12/2000
JP 2003310672 A 11/2003
(Continued)

OTHER PUBLICATIONS

Communication dated Jun. 24, 2014 issued by the European Patent Office in counterpart European Patent Application No. 14159064.6.
(Continued)

*Primary Examiner* — Daryl Pope
(74) *Attorney, Agent, or Firm* — Sughrue Mion, PLLC (57) ABSTRACT A medical alarm system includes: a bedside monitor which is configured to transmit alarm information when an abnormality is detected in measured biological information of a patient; a position information measuring device which is configured to transmit medical person position information when position information of a medical person is measured; and an information displaying device which is configured to receive and display the alarm information and the medical person position information. The information displaying device includes an alarm information displaying section and a medical person position information displaying section. When receiving the alarm information, the information displaying device displays the alarm information in the alarm information displaying section and the medical person position information in the medical person position information displaying section.

7 Claims, 5 Drawing Sheets (51) Int. Cl.
*A61B 5/00* (2006.01)
*G08B 25/00* (2006.01)
*G06F 19/00* (2011.01)
*G06K 9/00* (2006.01)

(56) References Cited

U.S. PATENT DOCUMENTS

| | | |
|---|---|---|
| 5,699,038 A | 12/1997 | Ulrich et al. |
| 2006/0049936 A1 | 3/2006 | Collins, Jr. et al. |
| 2007/0156031 A1* | 7/2007 | Sullivan et al. ............... 600/300 |
| 2008/0094207 A1 | 4/2008 | Collins, Jr. et al. |
| 2010/0079276 A1 | 4/2010 | Collins, Jr. et al. |
| 2011/0001605 A1 | 1/2011 | Kiani et al. |
| 2011/0043366 A1 | 2/2011 | Osone et al. |
| 2012/0092135 A1 | 4/2012 | Collins, Jr. et al. |
| 2012/0119890 A1 | 5/2012 | Collins, Jr. et al. |
| 2012/0223821 A1 | 9/2012 | Collins, Jr. et al. |
| 2012/0323090 A1 | 12/2012 | Bechtel et al. |
| 2014/0009271 A1 | 1/2014 | Collins, Jr. et al. |
| 2014/0018650 A1 | 1/2014 | Lord et al. |

FOREIGN PATENT DOCUMENTS

| | | |
|---|---|---|
| JP | 2007228982 A | 9/2007 |
| JP | 2008113679 A | 5/2008 |
| JP | 2011-041769 A | 3/2011 |
| WO | 2012/131546 A2 | 10/2012 |

OTHER PUBLICATIONS

Communication dated Mar. 14, 2016 issued by the Chinese Patent Office in a counterpart Chinese Patent Application No. 201410087905.7.

Communication from the Japanese Patent Office issued on May 10, 2016 in corresponding Japanese Patent Application No. 2013-048666.

* cited by examiner

MEDICAL ALARM SYSTEM AND MEDICAL ALARM INDICATOR

CROSS-REFERENCE TO RELATED APPLICATION(S)

This application is based upon and claims the benefit of priority from prior Japanese patent application No. 2013-048666, filed on Mar. 12, 2013, the entire contents of which are incorporated herein by reference.

BACKGROUND

The presently disclosed subject matter relates to a medical alarm system and medical alarm indicator for notifying of alarm information of a patient.

An alarm apparatus has been developed which measures biological information of a patient, which, when an abnormality occurs in the biological information, causes a bedside monitor to generate an alarm signal, and which, based on the alarm signal, outputs an alarm sound to inform of the abnormality. When an alarm sound is generated, a medical person knows that an abnormality occurs, and rushes to the patient to perform a treatment for the abnormality.

A medical person is often in charge of a plurality of patients. Therefore, there may arise a case where alarm sounds are output from a plurality of patients at overlapping timings. In such a case, there occur disadvantages such as that notifications by making a single alarm sound cause the sounds to overlap with each other to be hardly heard, and that the levels of the alarm sounds are suppressed by an operation of, for example, reducing the sound volume, and the alarms fail to be noticed. In the case where only audible notifications are performed, a situation may occur where the medical person cannot promptly determine which one of treatments each corresponding to the alarm sounds should be preferentially performed. Moreover, an inefficient situation may occur where two or more medical persons rush in response to the same alarm sound, i.e., to the identical patient.

To comply with this, JP-A-2011-041769 discloses a biological information monitoring system in which, in order to prevent a situation such as where an alarm is not noticed from occurring, and to ensure safety, alarms are performed by using different independent sounds or displays.

In the biological information monitoring system disclosed in JP-A-2011-041769, although it is possible to prevent a situation such as where an alarm is not noticed from occurring, the system is not always sufficient in view of that a medical person can promptly and efficiently perform a treatment for an alarm sound. In the biological information monitoring system disclosed in JP-A-2011-041769, a message is displayed in addition to the output of an alarm sound. However, the contents of a message are simply a notification that an alarming state occurs, and insufficient for enabling a medical person to perform a prompt and efficient treatment.

SUMMARY

The presently disclosed subject matter may provide a medical alarm system and medical alarm indicator which, in response to generation of alarm information, enable a medical person to perform a treatment on the patient promptly and efficiently.

The medical alarm system may comprise: a bedside monitor which is configured to transmit alarm information when an abnormality is detected in measured biological information of a patient; a position information measuring device which is configured to transmit medical person position information when position information of a medical person is measured; and an information displaying device which is configured to receive and display the alarm information and the medical person position information, wherein the information displaying device includes an alarm information displaying section and a medical person position information displaying section, and, when receiving the alarm information, the information displaying device displays the alarm information in the alarm information displaying section and the medical person position information in the medical person position information displaying section.

The position information measuring device may measure the position information of the medical person based on detection of an IC tag carried by the medical person.

The position information measuring device may measure the position information of the medical person based on face recognition of the medical person.

The information displaying device may be installed on a corridor side of an inlet of a patient room.

Each of the alarm information displaying section and the medical person position information displaying section may be a visible displaying unit.

The medical alarm system may further comprise a central monitor which is connected to a plurality of the bedside monitor through a network, and which is configured to centrally manage states of patients, wherein the alarm information and medical person position information of the patients may be displayed on the central monitor through the network.

The medical alarm indicator may include a medical person position information displaying section in which position information of a medical person is displayed.

DETAILED DESCRIPTION OF EXEMPLARY EMBODIMENTS

Hereinafter, embodiments of the medical alarm system of the presently disclosed subject matter will be described with reference to the accompanying drawings.

(First Embodiment)

Figure 1:
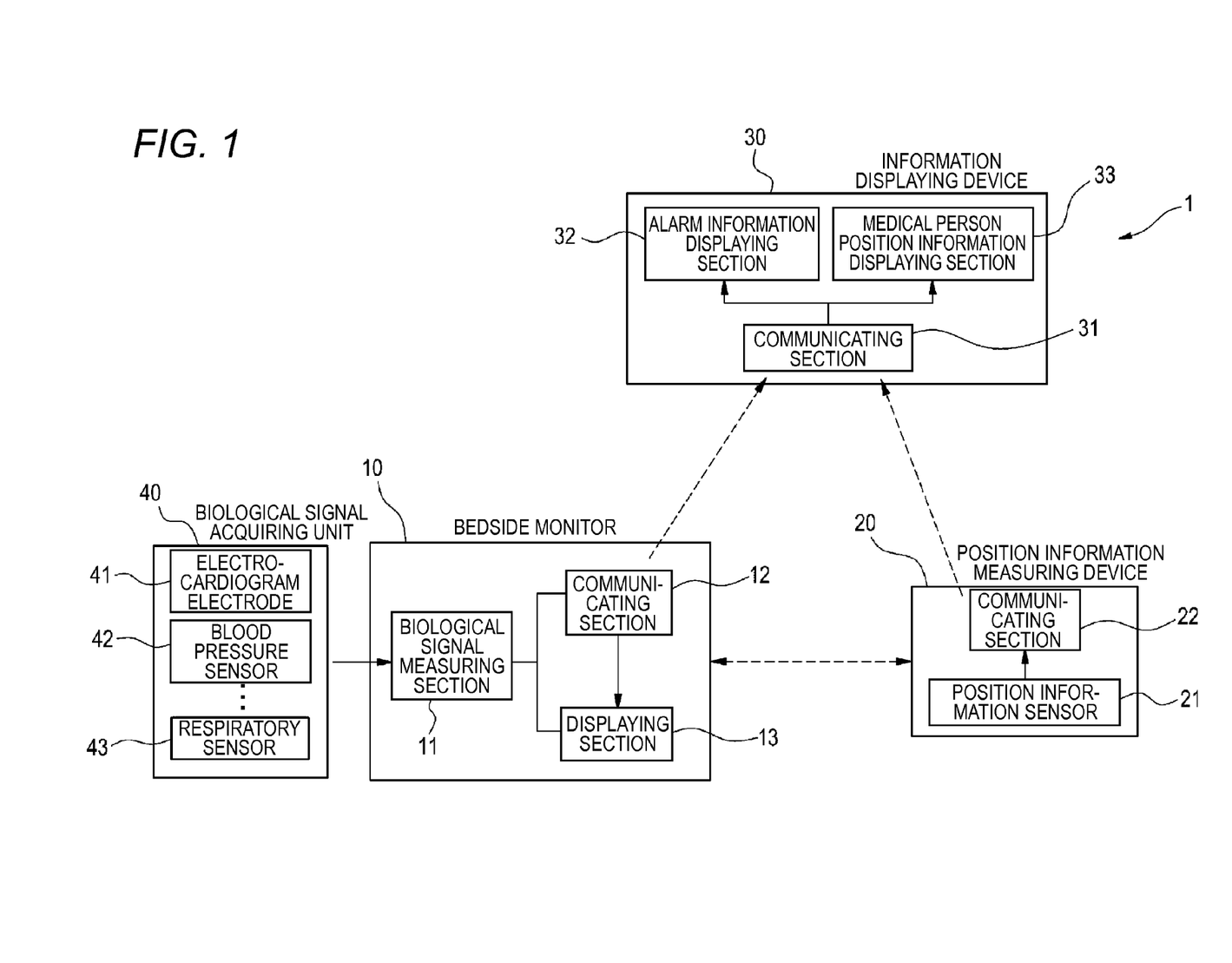
FIG. 1 is a block diagram illustrating the functional configuration of a medical alarm system of a first embodiment of the presently disclosed subject matter.

FIG. 1 illustrates the functional configuration of a medical alarm system 1 of a first embodiment.

The medical alarm system 1 may include: a biological information displaying device (bedside monitor) 10 which measures biological information of a patient; a position information measuring device 20 which measures position information of a medical person; and an information displaying device (indicator) 30 which displays information measured by the bedside monitor 10 and the position information measuring device 20.

The bedside monitor 10 is a device which, when it is determined that an abnormality occurs in measured biological information of the patient, transmits alarm information, and includes a biological signal measuring section 11, a communicating section 12, and a displaying section (displaying screen) 13.

The biological signal measuring section 11 measures the value of acquired biological information, and determines whether an abnormality occurs or not. Specifically, a comparing and determining unit disposed in the biological signal measuring section 11 compares the measured value of biological information with a predetermined threshold, and, in the case where the measured value exceeds or falls below the threshold, determines that an abnormality occurs. In the case where, as a result of the determination, it is determined that an abnormality occurs, the section supplies alarm information notifying of it, to the communicating section 12. The biological signal measuring section 11 outputs the measured biological information to the displaying section 13 in real time.

The communicating section 12 wirelessly transmits the alarm information output from the biological signal measuring section 11, to the information displaying device 30. The communicating section 12 wirelessly transmits an abnormality occurrence signal notifying of an occurrence of an abnormality, to the position information measuring device 20. Moreover, the communicating section 12 receives medical person position information which is wirelessly transmitted from the position information measuring device 20, and supplies the received medical person position information to the displaying section 13.

The displaying section 13 is a displaying screen which displays the biological signal of the patient that is supplied from the biological signal measuring section 11, and may be configured by, for example, a liquid crystal screen. The displaying section 13 further displays the alarm information supplied from the biological signal measuring section 11, and the medical person position information supplied from the communicating section 12. The contents of the display will be described later with reference of FIG. 3A.

A biological signal acquiring unit 40 for measuring biological information of the patient is connected to the bedside monitor 10. Specific examples of the biological signal acquiring unit 40 are various sensors such as electrocardiogram electrodes 41, a blood pressure sensor 42, and a respiratory sensor 43. The biological information acquired by the biological signal acquiring unit 40 is supplied to the biological signal measuring section 11 of the bedside monitor 10.

The position information measuring device 20 is a device which, when the position information of a medical person is measured, transmits the medical person position information, and includes a position information sensor 21 and a communicating section 22.

The position information sensor 21 is a unit for detecting and measuring the position information of a medical person. The position information of a medical person can be detected by, for example, measuring individual identification information of an IC tag by RFID (Radio Frequency IDentification). While a medical person carries an IC tag, when the medical person passes through a predetermined gate, the identification information is measured, and the position information of the medical person is acquired. The position information sensor 21 supplies the measured position information of the medical person, as the medical person position information to the communicating section 22.

As another method of acquiring position information of a medical person, for example, a camera disposed in a predetermined gate or the like may be used, and the information may be acquired by image processing of recognizing the face of the person.

The communicating section 22 wirelessly transmits the medical person position information supplied from the position information sensor 21, to the bedside monitor 10 and the information displaying device 30. The wireless transmission is performed each time when the medical person position information is sullied from the position information sensor 21. Also when the abnormality occurrence signal notifying of an occurrence of an abnormality is transmitted from the bedside monitor 10, the communicating section 22 wirelessly transmits the medical person position information which is detected at this time, to the information displaying device 30.

The medical person position information which is wirelessly transmitted to the information displaying device 30 may be directly transmitted from the communicating section 22 to the information displaying device 30. Alternatively, after the medical person position information is transmitted from the communicating section 22 to the bedside monitor 10, the information may be transmitted from the communicating section 12 of the bedside monitor 10 to the information displaying device 30.

The information displaying device 30 is an indicator which displays alarm information and medical person position information, and may include a communicating section 31, an alarm information displaying section 32, and a medical person position information displaying section 33.

The communicating section 31 receives the alarm information transmitted from the bedside monitor 10, and supplies the received alarm information to the alarm information displaying section 32. The communicating section 31 further receives the medical person position information transmitted from the position information measuring device 20, and supplies the received medical person position information to the medical person position information displaying section 33.

The alarm information displaying section 32 is a displaying section which displays the alarm information supplied from the communicating section 31. In accordance with the contents of the alarm information, the alarm information displaying section 32 may visibly display the information by, for example, lighting or blinking an indicator lamp, or changing the color of the indicator lamp.

The medical person position information displaying section 33 is a displaying section which displays the medical person position information supplied from the communicating section 31. In accordance with the contents of the information, the medical person position information displaying section 33 may visibly display the information by, for example, lighting or blinking an indicator lamp, or changing the color of the indicator lamp.

As described above, upon receiving alarm information from the bedside monitor 10, the information displaying device 30 causes the received alarm information to be displayed in the alarm information displaying section 32, and further the medical person position information received from the position information measuring device 20, to be displayed in the medical person position information displaying section 33.

In the kinds of abnormalities to be notified by the alarm information, in addition to an abnormality of biological information of a patient, a technical alarm which occurs in the case of detachment of an electrode, a failure in the attaching state of a sensor, or a high noise level, a nurse call which is used for notifying of an abnormality by a patient himself or herself, and the like may be included.

Figure 2:
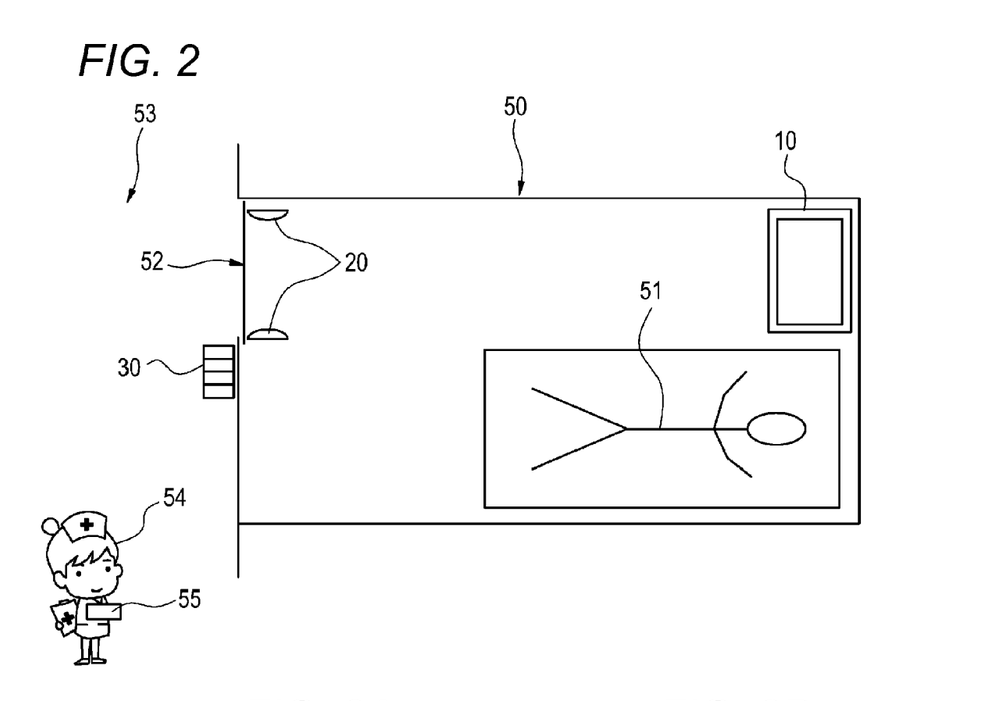
FIG. 2 is a diagram schematically illustrating an example of installation of the medical alarm system of FIG. 1.

FIG. 2 schematically illustrates a specific example of installation of the medical alarm system 1.

The specific example illustrates the case where the medical alarm system 1 is installed in a patient room (private room) 50 where one patient 51 stays. As illustrated in FIG. 2, the bedside monitor 10, the position information measuring device 20, and the information displaying device 30 are installed in the patient room 50. The position information measuring device 20 is installed in the inlet 52 of the patient room 50. The position information measuring device 20 is requested to be installed in a position where a medical person entering into or exiting from the patient room 50 can be surely detected. The information displaying device 30 is installed on a corridor 53 side of the inlet 52 of the patient room 50. Preferably, the information displaying device 30 is installed in a position where it can be checked easily and surely that an abnormality occurs in the patient 51 in the patient room 50.

When an abnormality occurs in the biological information of the patient 51 measured by the bedside monitor 10, an alarm information notifying that the abnormality occurs in the patient 51 is wirelessly transmitted from the bedside monitor 10 to the information displaying device 30. Moreover, an abnormality occurrence signal notifying of an occurrence of an abnormality is wirelessly transmitted from the bedside monitor 10 to the position information measuring device 20.

The position information measuring device 20 always detects a medical person entering into or exiting from the patient room 50. Each time when the existence of a medical person entering into or exiting from the patient room 50 is detected, medical person position information notifying that entering into the patient room 50 is performed, or that exiting from the patient room 50 is performed is wirelessly transmitted from the position information measuring device 20 to the information displaying device 30 and the bedside monitor 10. When the position information measuring device 20 receives the abnormality occurrence signal notifying of an occurrence of an abnormality from the bedside monitor 10, the medical person position information at the timing of the reception is wirelessly transmitted from the position information measuring device 20 to the information displaying device 30 and the bedside monitor 10.

As described with reference to FIG. 1, the medical person position information which is wirelessly transmitted from the position information measuring device 20 to the information displaying device 30 may be directly transmitted from the position information measuring device 20 to the information displaying device 30, or, after transmitted from the position information measuring device 20 to the bedside monitor 10, the information may be transmitted from the bedside monitor 10 to the information displaying device 30. In the latter case where the information is transmitted from the bedside monitor 10 to the information displaying device 30, the medical person position information may be transmitted together with the alarm information.

In the embodiment, the medical person 54 carries an identification tag (for example, a wireless IC tag) 55 in which individual identification information is recorded. The position information measuring device 20 detects the identification tag 55 of a medical person who enters into or exits from the patient room 50. In the case where the medical person 54 (the identification tag 55) entering into the patient room 50 is detected, medical person position information indicating that a medical person exists in the patient room 50 of the patient 51 in whom an abnormality occurs is wirelessly transmitted from the position information measuring device 20 to the information displaying device 30 and the bedside monitor. Similarly, in the case where the medical person 54 (the identification tag 55) exiting from the patient room 50 is detected, medical person position information indicating that a medical person does not exist in the patient room 50 of the patient 51 in whom an abnormality occurs is wirelessly transmitted.

On the information displaying device 30, when the alarm information is received, the alarm information transmitted from the bedside monitor 10, and the medical person position information transmitted from the position information measuring device 20 are displayed. These pieces of information are displayed with, for example, the light of the indicator lamp.

The embodiment illustrates the case of a private room. Also in the case where a plurality of patients are in one patient room, i.e., a plurality of bedside monitors 10 are installed in one patient room, alarm information and medical person position information are similarly informed.

Hereinafter, the contents of information displayed on the bedside monitor 10 and the information displaying device 30 will be described with reference to FIGS. 3A and 3B.

Figure 3A:
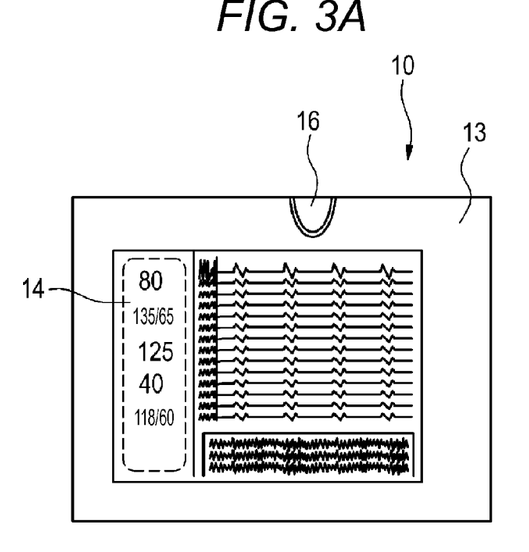
FIG. 3A is a view illustrating an example of a display of alarm information and medical person position information which are displayed on a bedside monitor.

As shown in FIG. 3A, in addition to biological information 14 measured from the patient 51, alarm information notifying of an abnormality of the biological information, and medical person position information notifying of the existence of a medical person are displayed in the displaying section 13 of the bedside monitor 10.

The alarm information is displayed in one of a plurality (in the embodiment, three) of stages in accordance with the emergency of the treatment to be applied to the patient 51 in whom an abnormality of biological information occurs. In the case of an abnormality of low emergency, for example, a display region 16 is displayed in blue, and, in the case of an abnormality of medium emergency, the display region 16 is displayed in yellow. In the case of an abnormality of significant emergency (requiring emergency treatment), the display region 16 is displayed in red.

Figure 3B:
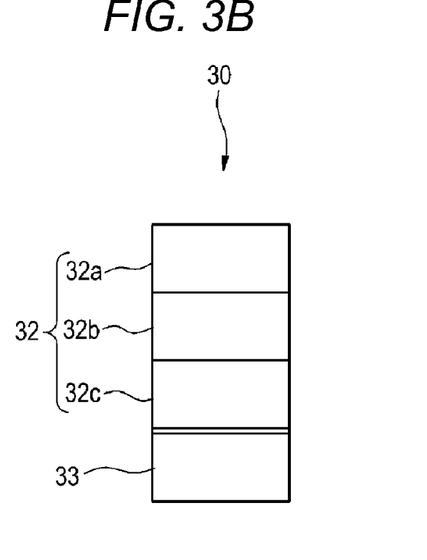
FIG. 3B is a view illustrating an example of an information displaying device.

As illustrated in FIG. 3B, the alarm information displaying section 32 and the medical person position information displaying section 33 are disposed in the information displaying device 30. For example, the displaying sections 32 and 33 have a post-like shape, and are separated from each other by vertical segmentation. The alarm information notifying of an abnormality of biological information is displayed in the alarm information displaying section 32. In the medical person position information displaying section 33, the medical person position information notifying of the existence of a medical person is displayed.

The alarm information displaying section 32 is divided into a plurality of displaying sections (in the embodiment, three displaying sections 32a, 32b, 32c), and configured so as to perform a display in accordance with the emergency of the treatment to be applied to the patient 51 in whom an abnormality of biological information occurs. When the contents of the alarm information indicate an abnormality of low emergency, for example, the displaying section 32c is displayed in blue, and, when the contents indicate an abnormality of medium emergency, the displaying section 32b is displayed in yellow, and, when the contents indicate an abnormality of significant emergency (requiring emergency treatment), the displaying section 32a is displayed in red.

The medical person position information displaying section 33 is displayed in different manners depending on whether or not a medical person exists in the patient room of the patient 51 in whom an abnormality of biological information occurs. In the case where a medical person exists in the patient room of the patient 51 in whom an abnormality of biological information occurs, for example, the lamp is lit, and, in the case where a medical person does not exist, the lamp is not lit.

Returning to FIG. 2, specific responses to be performed by the medical person 54 in the embodiment will be described. When an abnormality occurs in biological information of the patient 51, information (alarm information and medical person position information) related to the abnormality is displayed by light of the indicator lamp on the information displaying device 30. At this time, an alarm sound generates. The medical person 54 who is in the corridor 53 at the occurrence of the abnormality can view the alarm information (the color of the light of the indicator lamp) which is displayed in the alarm information displaying section 32 of the information displaying device 30, and know whether the emergency of the treatment to be applied is significant or insignificant. Moreover, the medical person 54 can view the medical person position information (the lighting or not lighting of the indicator lamp) which is displayed in the medical person position information displaying section 33 of the information displaying device 30, and know whether or not another medical person exists in the patient room of the patient 51 in whom the abnormality of biological information occurs, i.e., whether or not response to the occurrence of the abnormality in the patient 51 in whom the abnormality of biological information occurs is performed.

In the case where the medical person position information displaying section 33 is not lit, the medical person 54 can know that a treatment is not performed on the patient 51 in whom the abnormality of biological information occurs, and promptly rush to the patient 51 in whom the abnormality of biological information occurs. When the medical person 54 (the identification tag 55) enters into the patient room, the entering is detected by the position information measuring device 20, and the medical person position information displaying section 33 is lit. Then, the medical person 54 operates an alarm cancel button disposed in the bedside monitor 10 to cancel the alarming state. As a result, another medical person(s) who thereafter rushes to the patient room can view the information displaying device 30 disposed in the inlet of the patient room of the patient 51, and determine easily and promptly that a treatment has been applied to the patient 51 in whom the abnormality of biological information occurs. Therefore, inefficient situations such as where two or more medical persons rush to the same patient can be avoided, and the other medical person(s) can rush to another patient(s).

As described above, when an abnormality occurs in the patient, both the alarm information indicating the emergency of the treatment, and the medical person position information indicating whether or not a medical person exists in the patient room of the patient in whom an abnormality of biological information occurs are displayed on the information displaying device 30 installed in the inlet 52 of the patient room 50. Therefore, it is possible to promptly and correctly determine whether the medical person must rush to the patient or not. In accordance with the emergency of the alarm, it is possible to promptly and correctly determine the priorities of patients to whom medical persons must rush. Therefore, inefficient situations such as where two or more medical persons rush to the same patient can be avoided.

The position information of a medical person is measured by detection of the identification tag 55 such as a wireless IC tag, or face recognition of the medical person, and hence it is possible to promptly and correctly measure the position information of the medical person.

The information displaying device (indicator) 30 is installed in the inlet 52 (on the corridor side of the inlet 52) of the patient room 50. Therefore, a medical person can easily and correctly know the display contents.

(Second Embodiment)

Figure 4:
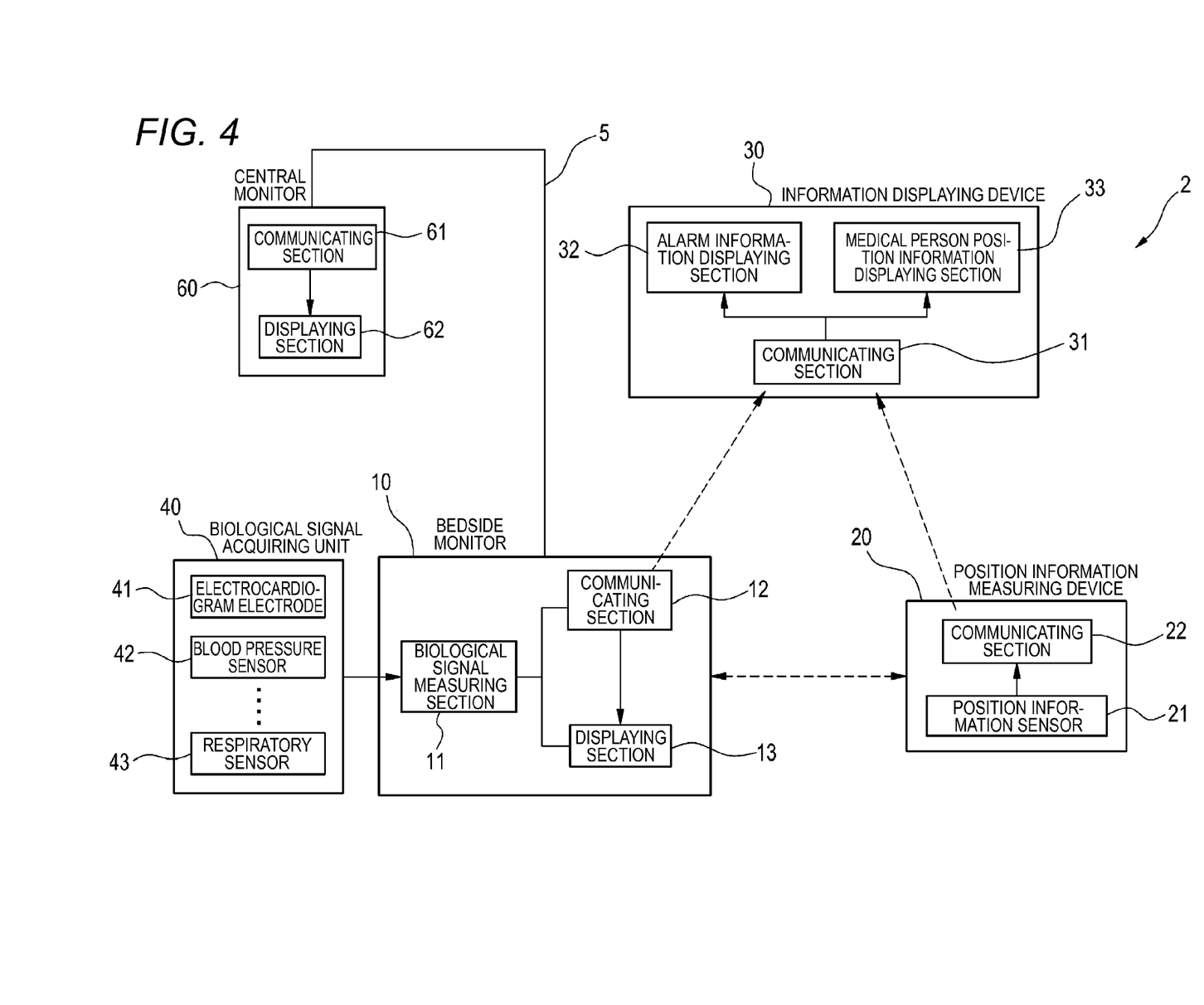
FIG. 4 is a block diagram illustrating the functional configuration of a medical alarm system of a second embodiment of the presently disclosed subject matter.

FIG. 4 illustrates the functional configuration of a medical alarm system 2 of a second embodiment.

The medical alarm system 2 has a configuration where a central monitor 60 is connected to the bedside monitors 10 through a network 5 (a LAN or the like), and information of the bedside monitors 10 is centrally managed through the network 5 by the central monitor 60. The medical alarm system 2 is different in these points from the medical alarm system 1 of the first embodiment. In the following description of the second embodiment, components identical with or similar to those of the first embodiment are denoted by the same reference numerals, and their detailed description is omitted.

The biological information of the corresponding patient which is measured by each of the bedside monitors 10, the alarm information which is output when an abnormality occurs in the biological information of the patient, and the medical person position information which is measured by the position information measuring device 20 are transmitted from the communicating section 12 of the bedside monitor 10 to the central monitor 60 through the network 5.

The central monitor 60 is a monitor which is connected to the plurality of bedside monitors 10 through the network 5, which centrally manages monitoring of the states of patients, and which is installed in a nurses' station, a waiting room for doctors, or the like. As shown in FIG. 4, the central monitor 60 may include a communicating section 61 and a displaying section 62.

The communicating section 61 receives the biological information, alarm information, and medical person position information which are transmitted from the bedside monitors 10, and supplies the received pieces of information to the displaying section 62.

The displaying section 62 is a displaying screen which displays the information which is supplied from the communicating section 61, and may be configured by, for example, a liquid crystal screen. Information of all the bedside monitors 10 connected through the network 5 can be displayed in the displaying section 62, and their display modes can be selected on the side of the central monitor. For example, biological information of a patient of the designated patient room can be displayed, or the patient room from which alarm information is output, the names of the patients in the room, and the like can be displayed.

Figure 5:
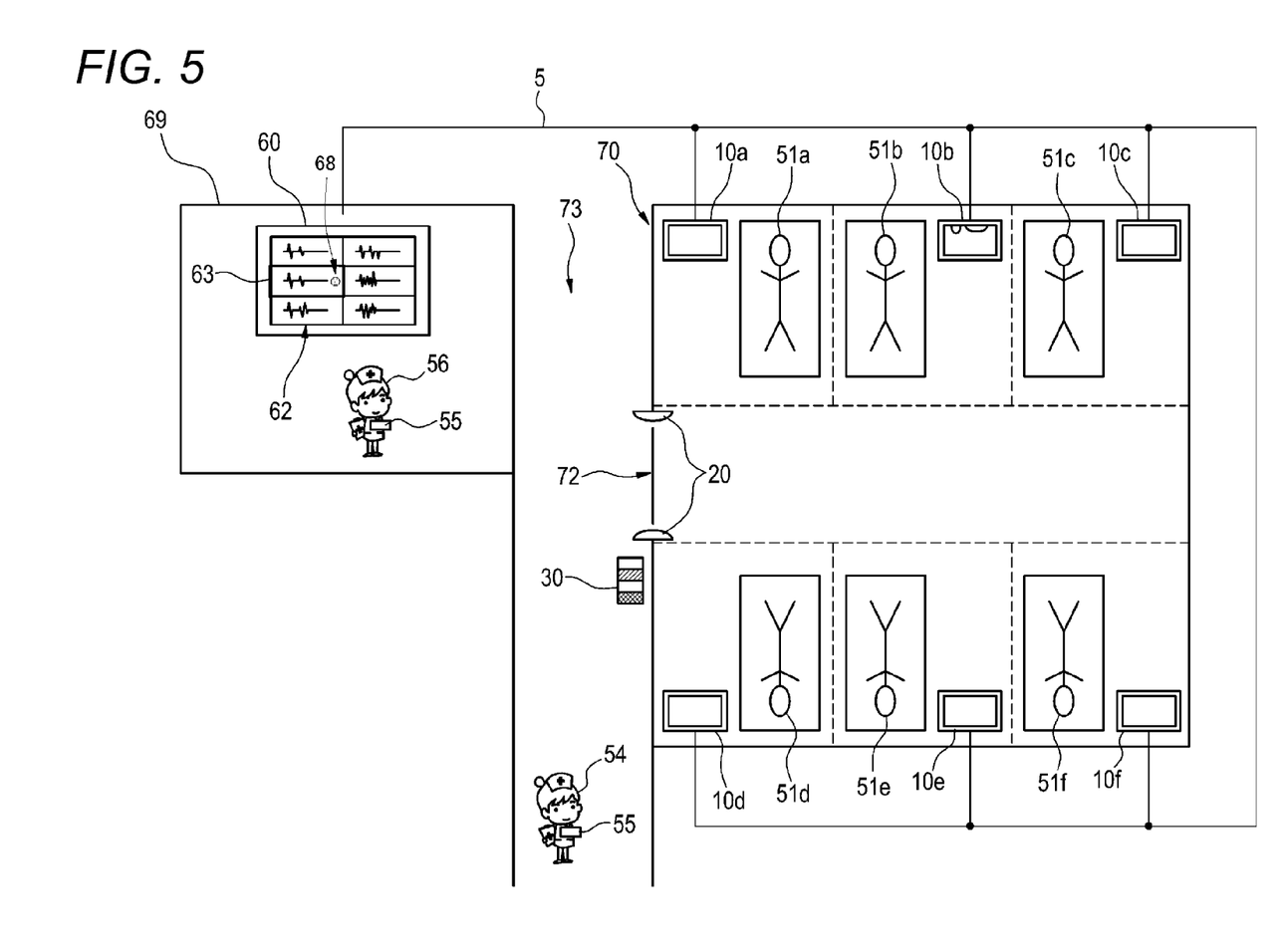
FIG. 5 is a diagram schematically illustrating a configuration example of the medical alarm system of FIG. 4.

FIG. 5 schematically illustrates a specific example of installation of the medical alarm system 2.

The specific example shows the medical alarm system 2 in which bedside monitors 10a, 10b, . . . , 10f in a patient room (ward) 70 where a plurality of patients 51a, 51b, . . . , 51f stay are connected to the central monitor 60 in a nurses' station 69 through the network 5.

In the patient room 70, the bedside monitors 10a, 10b, . . . , 10f, the position information measuring device 20, and the information displaying device 30 are installed. The position information measuring device 20 is installed in the inlet 72 of the patient room 70. The information displaying device 30 is installed on a corridor 73 side of the inlet 72.

When an abnormality occurs in the biological information of the patients 51a, 51b, . . . , 51f measured by the bedside monitors 10a, 10b, . . . , 10f, an alarm information notifying of the abnormality is wirelessly transmitted from the bedside monitor which detects the abnormality, to the information displaying device 30, and transmitted to the central monitor 60 through the network 5. Moreover, an abnormality occurrence signal notifying of an occurrence of an abnormality is wirelessly transmitted from the bedside monitor which detects the abnormality, to the position information measuring device 20. The following description of the embodiment will be made assuming that an abnormality occurs in the biological information of the patient 51b.

Upon receiving the abnormality occurrence signal notifying that an abnormality occurs from the bedside monitor 10b, the position information measuring device 20 wirelessly transmits medical person position information at the timing of the reception, to the information displaying device 30 and at least the bedside monitor 10b. The medical person position information which is transmitted to the bedside monitor 10b is transmitted to the central monitor 60 through the network 5.

The alarm information transmitted from the bedside monitor 10b, and the medical person position information transmitted from the position information measuring device 20 are displayed on the information displaying device 30.

The occurrence of an abnormality in the patient 51b of the patient room 70, the emergency of the treatment for the abnormality, and information indicating whether a medical person exists in the patient room 70 or not are displayed in the displaying section 62 of the central monitor 60.

In the displaying section 62, for example, biological information of the patients in the patient room 70 is displayed while dividing the information into respective patient regions. The frame of the region where the biological information of the patient 51b from whom an alarm is generated is highlighted by a thick line 63 of a color corresponding to the emergency of the alarm. The highlighting by the thick line 63 illustrates the alarm occurrence in the patient 51b. The situation where a medical person has rushed to the patient room 70 is indicated by a face mark 68 shown in the region enclosed by the thick line 63. A medical person 56 who is in the nurses' station 69 views the information displayed on the central monitor 60, and can determine promptly and correctly from which one of patient rooms alarm information is transmitted, the emergency of the treatment to be applied to the patient 51b in whom an abnormality of biological information occurs, whether a medical person exists in the patient room or not, and the like.

Figure 6:
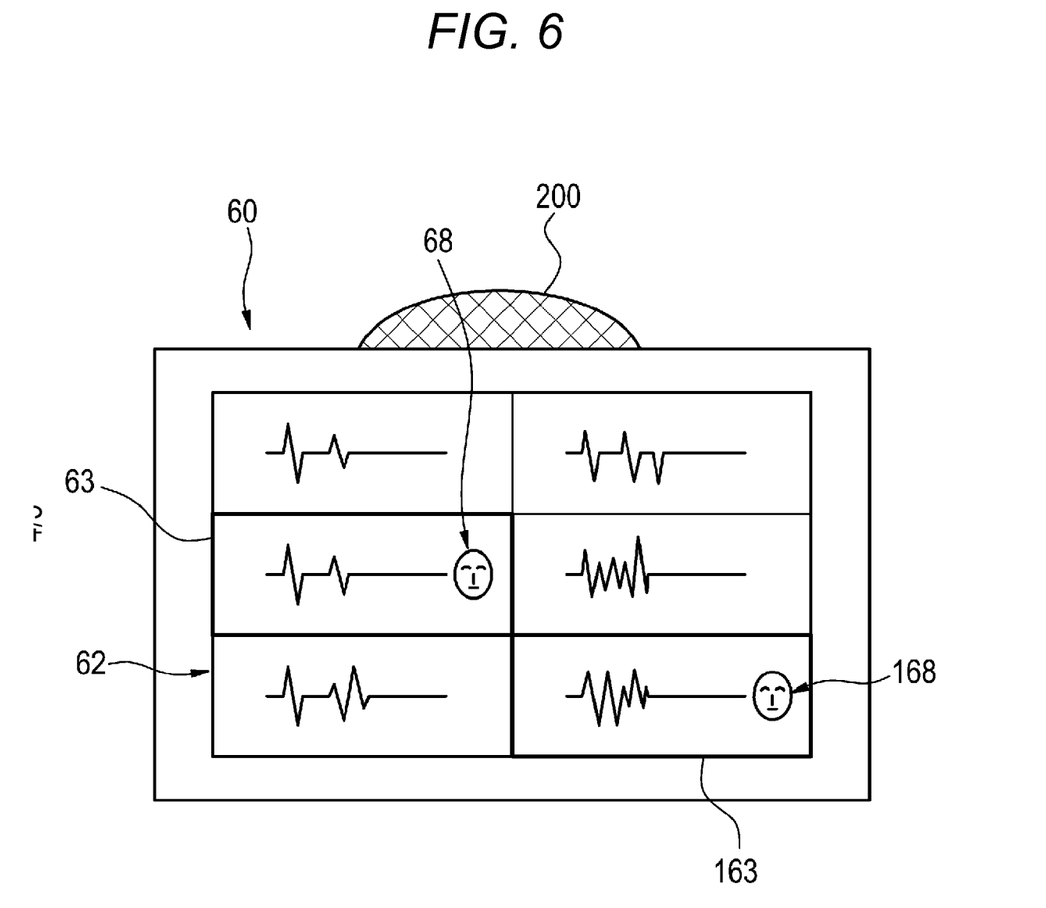
FIG. 6 is a view illustrating an example of display information displayed on a central monitor.

In the case of a ward such as shown in FIG. 5, there may arise a situation where alarm information is transmitted from two or more patients. FIG. 6 illustrates information displayed on the central monitor 60 in the case where, in the patient room 70, alarm information is transmitted at overlapping timings from the patient 51b and the patient 51f.

Information indicating that an abnormality occurs in the patients 51b and 51f in the patient room 70, the emergencies of treatments for the abnormalities, and whether a medical person is in the patient room 70 or not are displayed in the displaying section 62. In the displaying section 62, for example, the outline of the region where the biological information of the patient 51b from whom the alarm is generated is highlighted by the thick line 63 of a color (in the example, yellow) corresponding to the emergency of the alarm. Moreover, the situation where a medical person has rushed to the patient room 70 is indicated by the face mark 68 shown in the region enclosed by the thick line 63. In the displaying section 62, similarly, the outline of the region where the biological information of the patient 51f from whom the alarm is generated is highlighted by the thick line 163 of a color (in the example, red) corresponding to the emergency of the alarm. Moreover, the situation where a medical person has rushed to the patient room 70 is indicated by the face mark 168 shown in the region enclosed by the thick line 163.

In the case where alarm information is transmitted from two patients, it is set that, between the patients 51b and 51f in whom an abnormality of biological information occurs, the alarm information of the one in whom the emergency of the treatment is higher is displayed on the information displaying device 30. In the example, the emergency of the patient 51b is medium, and that of the patient 51f is significant. Therefore, the alarm information of the patient 51f is displayed on the information displaying device 30. An alarm lamp 200 of the central monitor 60 is lit with a color (in the example, red) corresponding to the emergency of the patient 51f.

When a medical person views the information displayed on the central monitor 60, the medical person can determine promptly and correctly that alarm information is transmitted from a plurality of patients (patients 51b and 51f), that the priority of the treatment on the patient 51f is higher, and whether or not a medical person exists in the patient room 70 where the patient 51f stays.

Preferably, the display mode of the central monitor 60 in the case where alarm information is transmitted from two or more patients as described above may be set so that, in the case where the treatment on the patient 51f in whom an abnormality of biological information occurs is started, the light-off state of the medical person position information displaying section 33 in FIG. 6 is maintained, and the alarm information of the alarm information displaying section 32 is changed to the information of the patient 51b in whom an abnormality of biological information occurs. According to the configuration, even when alarm information is transmitted from two or more patients, it is possible to surely prevent treatments to be applied on the patients in whom an abnormality of biological information occurs, from failing to be performed.

Specific responses to be performed by the medical person 54 in the embodiment are similar to those described with respect to the first embodiment.

According to the configuration, when a medical person views information displayed on the central monitor 60, or the medical person position information of the information displaying device 30 installed in the inlet of a patient room, the medical person can know whether another medical person has already reached the patient or not. Therefore, it is possible to prevent an inefficient situation where a plurality of medical persons rush to the same patient, from occurring.

Alternatively, a portable terminal carried by a medical person may be used as the information displaying device 30. A bedside monitor may wirelessly transmit alarm information and medical person position information, and the pieces of information may be transmitted to the portable terminal carried by a medical person through a server. For example, information which relates to the abnormality occurrence, and which is similar to that on the central monitor 60 illustrated in FIG. 6 is displayed on a displaying screen of the portable terminal. When the medical person views the terminal carried by the medical person, the medical person can know easily and correctly the displayed contents, and determine promptly and correctly the emergency of the treatment to be applied to the patient in whom an abnormality of biological information occurs, whether a medical person performs the treatment or not, and the like.

Although the presently disclosed subject matter has been described in detail and with reference to the specific embodiments, it is obvious to those skilled in the art that various changes and modifications can be made without departing from the spirit and scope of the presently disclosed subject matter.

According to an aspect of the presently disclosed subject matter, when the information displaying device is installed in a place which attracts notice of a medical person (for example, the inlet of a patient room), or when information is displayed on the portable terminal carried by the medical person, it is possible to know easily and promptly whether a medical person is in a place of the patient who generates an alarm. Therefore, a treatment on the patient can be performed promptly and efficiently.

What is claimed is:

1. A medical alarm system comprising:
   a bedside monitor which is configured to transmit alarm information when an abnormality is detected in measured biological information of a patient;
   a position information measuring device which is configured to transmit medical person position information when position information of a medical person is measured; and
   an information displaying device which is configured to receive and display the alarm information and the medical person position information, wherein
   the information displaying device includes an alarm information displaying section and a medical person position information displaying section,
   when receiving the alarm information, the information displaying device displays the alarm information in the alarm information displaying section and the medical person position information in the medical person position information displaying section, the alarm information displayed in the alarm information displaying section indicating an emergency of a treatment to be applied to a patient in whom an abnormality of biological information occurs, the medical person position information displayed in the medical person position information displaying section indicating whether or not a medical person exists in a patient room of the patient in whom the abnormality of the biological information occurs, and the alarm information and the medical person position information are concurrently displayed.

2. The medical alarm system according to claim 1, wherein the position information measuring device measures the position information of the medical person based on detection of an IC tag carried by the medical person.

3. The medical alarm system according to claim 1, wherein the position information measuring device measures the position information of the medical person based on face recognition of the medical person.

4. The medical alarm system according to claim 1, wherein the information displaying device is installed on a corridor side of an inlet of a patient room.

5. The medical alarm system according to claim 1, wherein each of the alarm information displaying section and the medical person position information displaying section is a visible displaying unit.

6. The medical alarm system according to claim 1, further comprising a central monitor which is connected to a plurality of the bedside monitor through a network, and which is configured to centrally manage states of patients, wherein
   the alarm information and medical person position information of the patients are displayed on the central monitor through the network.

7. A medical alarm indicator including a medical person position information displaying section in which position information of a medical person is displayed, the position information displayed in the medical person position information displaying section indicating whether or not the medical person exists in a patient room of a patient in whom an abnormality of biological information occurs,
   the medical alarm indicator including an alarm information displaying section in which alarm information is displayed, the alarm information displayed in the alarm information displaying section indicating an emergency of a treatment to be applied to the patient in whom the abnormality of the biological information occurs, and
   the alarm information and the position information being concurrently displayed.

* * * * *